(12) United States Patent
Fukumoto et al.

(10) Patent No.: US 7,818,054 B2
(45) Date of Patent: Oct. 19, 2010

(54) ACUPUNCTURE POINT POSITION EVALUATING APPARATUS

(75) Inventors: Takenori Fukumoto, Kanagawa (JP); Hisashi Akiyama, Kanagawa (JP)

(73) Assignee: Panasonic Corporation, Osaka (JP)

( * ) Notice: Subject to any disclaimer, the term of this patent is extended or adjusted under 35 U.S.C. 154(b) by 431 days.

(21) Appl. No.: 11/911,464

(22) PCT Filed: Apr. 13, 2006

(86) PCT No.: PCT/JP2006/307844
§ 371 (c)(1),
(2), (4) Date: Oct. 12, 2007

(87) PCT Pub. No.: WO2006/115072
PCT Pub. Date: Nov. 2, 2006

(65) Prior Publication Data
US 2009/0036798 A1     Feb. 5, 2009

(30) Foreign Application Priority Data
Apr. 21, 2005   (JP)   ............................. 2005-124291

(51) Int. Cl.
A61H 39/02   (2006.01)
A61B 5/05    (2006.01)
A61B 5/04    (2006.01)

(52) U.S. Cl. ..................... 600/548; 600/546; 600/547

(58) Field of Classification Search .................. 600/300, 600/306, 372, 382, 544, 545, 546, 547, 548, 600/554, 587; 607/1, 2, 3, 39, 40, 42, 44, 607/45, 46, 47, 53, 54, 55, 58
See application file for complete search history.

(56) References Cited
U.S. PATENT DOCUMENTS
5,339,827 A    8/1994  Masopust
(Continued)

FOREIGN PATENT DOCUMENTS
JP     2001-112843    4/2001
(Continued)

OTHER PUBLICATIONS
NIH Consensus Statement Nov 3-5, 1997; 15(5):1-34. [http://consensus.nih.gov/1997/1997acupuncture107html.htm].*
(Continued)

Primary Examiner—Max Hindenburg
Assistant Examiner—Jeffrey G Hoekstra
(74) Attorney, Agent, or Firm—Pearne & Gordon LLP

(57) ABSTRACT

An acupuncture point position evaluating apparatus in which a current generated in a current generating section is applied to measurement points of skin of a subject through current application electrodes. The applied current and a voltage generated in the skin by the current application are measured in a measuring section. In a frequency analyzing section, the measured current and the measured voltage are provided with frequency analysis, and skin impedance $Z(jf)$ in the respective measurement points is calculated. In a characteristics amount generating section, based on the frequency response of the skin impedance $Z(jf)$ in the measurement points, frequency response $K(f)=XZ(f)/RZ(f)$ as a ratio between real part $RZ(f)$ and imaginary part $XZ(f)$ of the skin impedance $Z(jf)$ are calculated. In a determining section, based on the difference of the frequency response $K(f)$, an acupuncture point position is determined from among the respective measurement points.

7 Claims, 3 Drawing Sheets

U.S. PATENT DOCUMENTS

| | | |
|---|---|---|
| 6,505,079 B1 | 1/2003 | Foster et al. |
| 2003/0009111 A1 | 1/2003 | Cory et al. |

FOREIGN PATENT DOCUMENTS

| | | |
|---|---|---|
| JP | 2003-180846 | 7/2003 |
| JP | 2004-337349 | 12/2004 |

OTHER PUBLICATIONS

Damijan Miklavcic et al., Electric properties of tissues, Wiley Encyclopedia of Biomedical Engineering, 2006, John Wiley & Sons, Inc. found at http://llbk.fe.uni-lj.si/pdfslwebt2OO6.pdf.*
International Search Report Dated Jun. 6, 2006.
European Search Report dated Oct. 14, 2009.

* cited by examiner

ACUPUNCTURE POINT POSITION EVALUATING APPARATUS

TECHNICAL FIELD

The present invention relates to an acupuncture point position evaluating apparatus that can noninvasively, objectively, and precisely determine acupuncture stimulation effects and a position of a stimulation point called acupuncture point in acupuncture treatment or the like.

BACKGROUND ART

Through the ages, it has been known that a small region with the skin resistance lower than that of the surrounding regions exists on the skin surface, and the distribution thereof comparatively well corresponds with the distribution of acupuncture points as a stimulation point in acupuncture treatment. Such a region with the skin resistance lower than that of the surrounding regions (referred to as skin resistance attenuation point) is used for treatment in Ryodoraku (good electroconductive meridian) autonomic nerve modulation method, a low frequency treatment apparatus and the like. Apparatuses searching for the skin resistance attenuation points are available in the market, and are practically used in clinical diagnosis and treatment.

In the past, in the apparatus searching for (determining) an acupuncture point as the skin resistance attenuation point, a method in which the skin DC resistances are measured as electric characteristics of the skin in and around the acupuncture point, and the acupuncture point is determined based on the difference thereof has been often used. However, in determining the acupuncture point by measuring the DC current resistance as above, for example, there are following problems. That is, the measurement results depend on a contact state of the measurement electrodes, or the measurement result is not able to be clearly differentiated from spontaneous change of the skin voltage, resulting in poor reliability and poor reproducibility of the measurement results.

Therefore, in recent years, the following method has been employed as a method to improve the reliability and the reproducibility of the measurement results. In such a method, as electric characteristics of the skin in and around an acupuncture point, a distribution on the complex plane of the frequency response of the skin impedance (skin impedance locus) is measured based on a voltage generated by applying an AC current to the skin in and around the acupuncture point, and the acupuncture point is determined based on the difference of the skin impedance locus. For example, out of 4 parameters characterizing the shape of the skin impedance locus (after-mentioned $Z_0$, $Z_\infty$, $\beta$, and $\tau_m$), the central relaxation time $\tau_m$ in Cole-Cole circular arc's law is noted as a parameter that does not largely depend on the contact state of the measurement electrodes and clearly reflects the electric characteristics difference between the acupuncture point and the other regions. Based on the difference of the parameter $\tau_m$, the acupuncture point is determined. Thereby, the problems included in the prior art can be avoided (for example, refer to the following Patent Document 1).

Patent Document 1: Japanese Patent Application Publication No. 2004-337349 (Abstract and claim 2)

In the prior art, in evaluating the electric characteristics difference between the acupuncture point and the other regions, the central relaxation time $\tau_m$ in Cole-Cole circular arc's law is calculated as a parameter characterizing the shape of the skin impedance locus. In the prior art, however, the following problems exist.

When the central relaxation time $\tau_m$ characterizing the shape of the skin impedance locus is calculated, the Cole-Cole circular arc's law should be satisfied in the frequency response of the skin impedance. However, the prior art has no means for confirming whether or not Cole-Cole circular arc's law is satisfied. Further, the central relaxation time $\tau_m$ should be inferred based on the measured skin impedance in a plurality of frequencies with the use of nonlinear least square method or the like. However, the procedure for inferring it is tangled, leading to a complicated hardware configuration, and thus such a method is not suitable for realizing a small size apparatus. Furthermore, to precisely infer the central relaxation time $\tau_m$, as shown in FIG. 4, it is necessary that the measured skin impedance data is distributed not in an unbalanced manner but uniformly on the skin impedance locus.

However, as shown in FIG. 5, the distribution of the skin impedance data measured on actual skin often partially exists on the impedance locus in an unbalanced manner. In addition, the distribution manner often largely varies according to each measurement point. In this case, to precisely infer the central relaxation time $\tau_m$ characterizing the shape of the skin impedance locus, it is necessary to measure the skin impedance in the wide range of frequencies including extremely low frequencies. In result, the time resolution is lowered. In addition, as the measurement target frequency becomes lower, the measurement is subject to disturbance due to temperature drift, human physical movement and the like, and thus it is difficult to assure the reliability and the reproducibility of the measurement result.

DISCLOSURE OF THE INVENTION

The present invention has been achieved to solve the above-described problems in the prior art. An object of the present invention is to provide an acupuncture point position evaluating apparatus that can determine an acupuncture point with the reliability and the reproducibility with the use of a simple hardware configuration.

In order to solve the foregoing conventional problems, according to the present invention, there is provided an acupuncture point position evaluating apparatus including: a current generating section for generating a current composed of at least one frequency component; an electrode system for almost concurrently applying an output current from the current generating section to a plurality of different measurement points on skin by a plurality of electrodes arranged on the skin of a living body; a current detector for detecting the current respectively applied to the plurality of measurement points; a measuring section for measuring the current detected by the current detector and a voltage generated in the skin of the plurality of measurement points by current application by the electrode system; a frequency analyzing section for performing frequency analysis for both the current and the voltage measured by the measuring section, and obtaining frequency response of a skin impedance in the respective measurement points; a characteristics amount generating section for generating a characteristics amount of the skin impedance in the respective measurement points based on the frequency response of the skin impedance in the plurality of measurement points that are analyzed by the frequency analyzing section; a determining section for determining an acupuncture point position based on the characteristics amount in the respective measurement points generated by the characteristics amount generating section; and a display means for displaying the characteristics amount in the respective measurement points generated by the characteristics amount generating section and the acupuncture point position determined by the determining section.

Accordingly, the procedure for calculating the characteristics amount used for evaluation becomes simple, and the reliability and the reproducibility of the measurement result can be improved more than those of the conventional example. In addition, the characteristics amount used for the evaluation has a correlativity with the conventionally noted central relaxation time $\tau_m$. Consequently, the acupuncture point can be determined based on the difference of the evaluation parameter that does not largely depend on the contact state of the measurement electrodes and clearly reflects the electric characteristics difference between the acupuncture point and the other regions.

According to the acupuncture point position evaluating apparatus of the present invention, the frequency analyzing section confirms whether or not Cole-Cole circular arc's law is satisfied in the frequency response of the skin impedance in the respective measurement points.

Accordingly, whether or not Cole-Cole circular arc's law is satisfied in the measured skin impedance can be confirmed, and the reliability and the reproducibility of the measurement result can be improved more than those of the conventional example.

According to the acupuncture point position evaluating apparatus of the present invention, the applied current generated in the current generating section includes one lowest frequency component and a frequency component as an integer multiple of the lowest frequency.

Accordingly, spectrum leakage to the adjacent frequencies when discrete Fourier transform is provided does not exist, and the lower limit of the time resolution is determined only depending on the lowest frequency. Therefore, the skin impedance locus can be measured with the high time resolution.

According to the acupuncture point position evaluating apparatus of the present invention, the current generating section can change a size of the frequency component included in the applied current for every frequency and for every measurement position.

Accordingly, an optimal signal to noise ratio can be secured for every frequency and for every measurement point, and the skin impedance locus can be precisely measured.

According to the acupuncture point position evaluating apparatus of the present invention, the characteristics amount generated in the characteristics amount generating section is a ratio between a real part and an imaginary part of the skin impedance in at least one frequency.

Accordingly, the procedure for inferring the parameter is not tangled.

According to the acupuncture point position evaluating apparatus of the present invention, out of each ratio between a real part and a imaginary part of the skin impedance in at least one frequency, the characteristics amount generating section selects a ratio of a frequency in which a difference thereof among the respective measurement points is significant as the characteristics amount.

Accordingly, the procedure for inferring the parameter is not tangled, and the reliability of determining the acupuncture point position in the determining section is more improved.

According to the acupuncture point position evaluating apparatus of the present invention, the characteristics amount generated in the characteristics amount generating section is a ratio between a real part and an imaginary part of the skin impedance in a lowest frequency included in the applied current.

Accordingly, the procedure for inferring the parameter is not tangled, and the acupuncture point position can be determined quickly.

According to the invention, whether or not Cole-Cole circular arc's law is satisfied in the measured skin impedance can be confirmed, and the procedure for calculating the characteristics amount used for evaluation can be realized with the use of the simple hardware configuration. Further, the reliability and the reproducibility of the measurement result can be improved more than those of the conventional example. In addition, the characteristics amount used for the evaluation has a correlativity with the conventionally noted central relaxation time $\tau_m$. Therefore, the acupuncture point can be determined based on the difference of the evaluation parameter that does not largely depend on the contact state of the measurement electrodes and clearly reflects the electric characteristics difference between the acupuncture point and the other regions. Consequently, the acupuncture point position apparatus with the higher reliability and the higher reproducibility can be provided with the use of the simple hardware configuration.

BEST MODE FOR CARRYING OUT THE INVENTION

Figure 1:
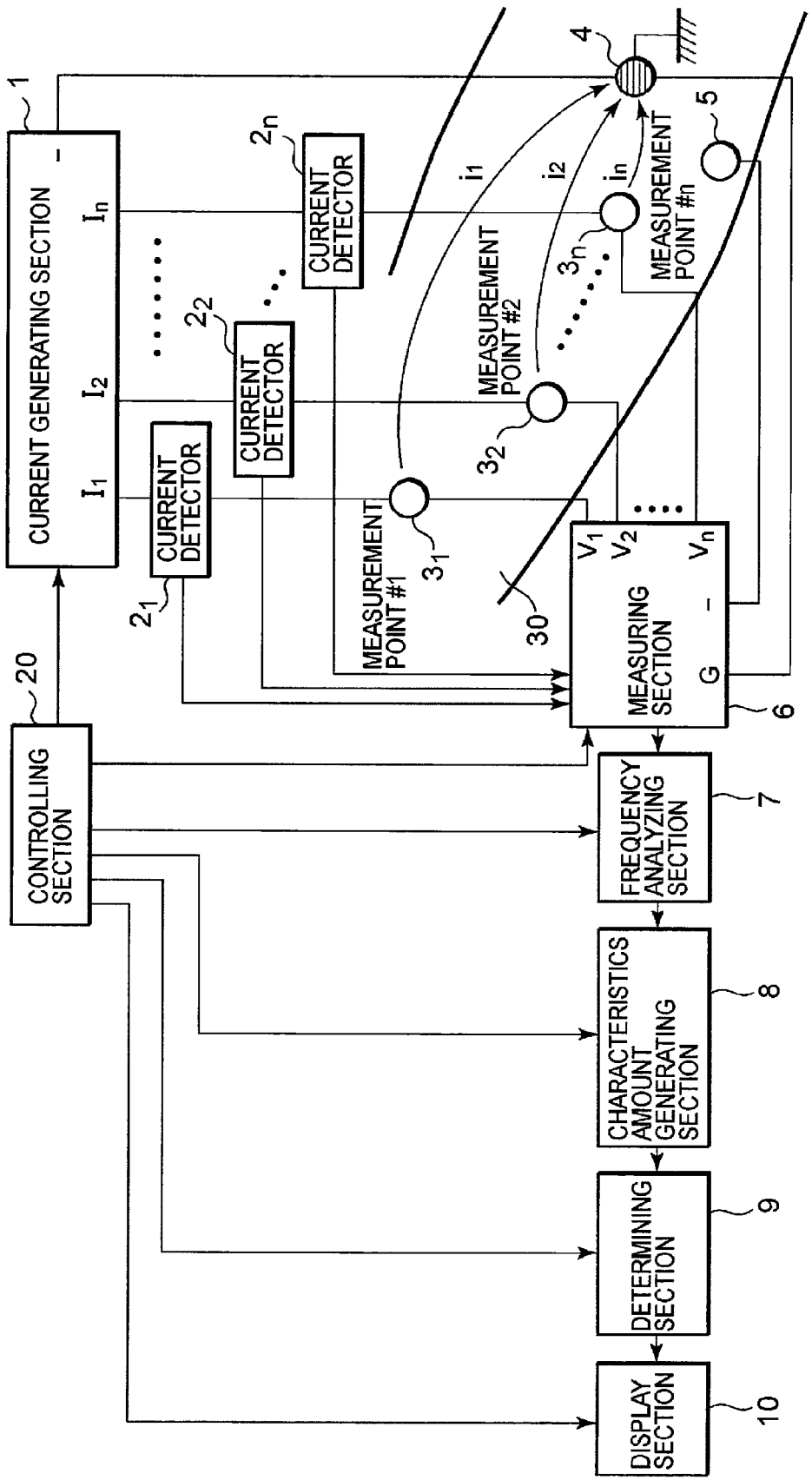
FIG. 1 is a block diagram showing a schematic structure in a first embodiment of the acupuncture point position evaluating apparatus of the present invention.

An embodiment of the present invention will be hereinafter described with reference to the figures. FIG. 1 is a block diagram showing a schematic structure of a first embodiment of the acupuncture point position evaluating apparatus of the present invention. AC currents $I_1$ to $I_n$ generated from a current generating section 1 are respectively applied to respective measurement points #1 to #n of skin 30 of a subject via current detectors $2_1$ to $2_n$ and current application electrodes $3_1$ to $3_n$, and then flow to an earth electrode 4. Voltage drop of voltages $V_1$ to $V_n$ in the skin between the current application electrodes $3_1$ to $3_n$ and a minus electrode 5 (−) that is generated by this current application is measured by a measuring section 6 based on an electric potential of the earth electrode 4 as a reference. The measuring method with the use of such an electrode system is called 3 electrode method. The method is often used for measuring a skin impedance directly under the current application electrodes $3_1$ to $3_n$, that is, directly under the measurement points #1 to #n.

Figure 2:
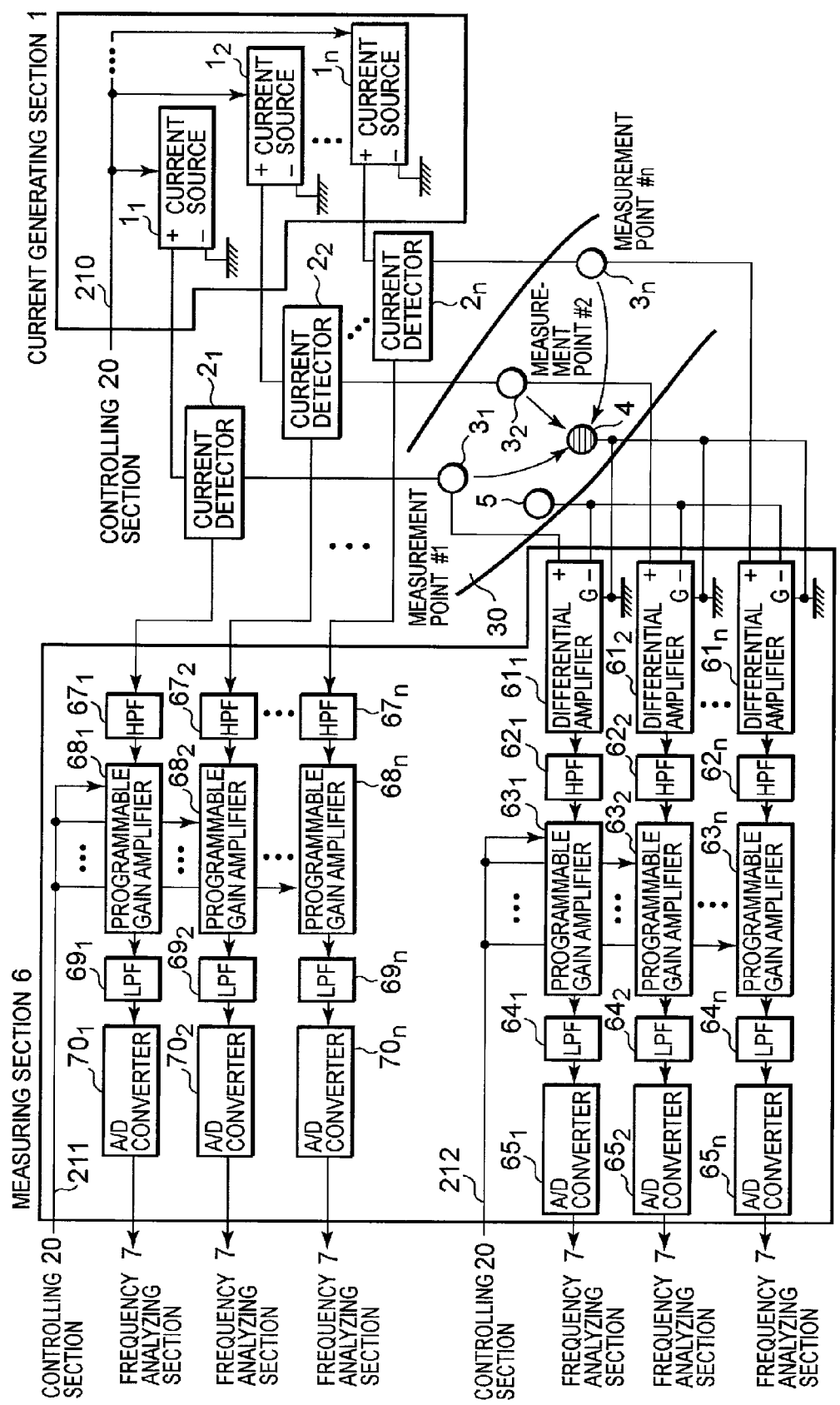
FIG. 2 is a block diagram showing a more detailed structural example of an electrode system and a measuring section of FIG. 1.

FIG. 2 shows a block diagram showing a more detailed structural example of the current generating section 1 and the measuring section 6. The current generating section 1 is composed of at least one of current sources $1_1$ to $1_n$. The current sources $1_1$ to $1_n$ generate the AC currents $I_1$ to $I_n$ that are respectively applied to the respective measurement points #1 to #n. The number of frequency components, the frequency, and the size included in the currents $I_1$ to $I_n$ generated from the respective current sources $1_1$ to $1_n$ can be set by a control signal 210 from a controlling section 20. The measuring section 6 is composed of at least one of differential amplifiers $61_1$ to $61_n$ for measuring the voltages $V_1$ to $V_n$ generated in the skin directly under the respective measurement points #1 to #n by current application, at least one of high pass filters (HPF) $62_1$ to $62_n$ (and $67_1$ to $67_n$), at least one of programmable gain amplifiers (PGA) $63_1$ to $63_n$ (and $68_1$ to $68_n$), at least one of low pass filters (LPF) $64_1$ to $64_n$ (and $69_1$ to $69_n$), and at least one of A/D converters $65_1$ to $65_n$ (and $70_1$ to $70_n$).

The voltages $V_1$ to $V_n$ generated in the skin of the measurement points #1 to #n by current application are respectively measured by the differential amplifiers $61_1$ to $61_n$. The measured voltages $V_1$ to $V_n$ include an unnecessary signal component not resulting from the current application. Such an unnecessary signal component hinders accurate frequency analysis in a frequency analyzing section 7. Therefore, an unnecessary low frequency component is removed respectively from output of the differential amplifiers $61_1$ to $61_n$ by the high pass filters (HPF) $62_1$ to $62_n$. The voltages $V_1$ to $V_n$ of the measurement points #1 to #n from which the unnecessary low frequency component is removed are respectively amplified by the programmable gain amplifiers $63_1$ to $63_n$ if necessary. Next, an unnecessary high frequency component is removed by the low pass filters $64_1$ to $64_n$.

The currents $I_1$ to $I_n$ applied to the skin of the measurement points #1 to #n are respectively measured by the current detectors $2_1$ to $2_n$. Unless the same signal processing as that for the voltages $V_1$ to $V_n$ in the measurement points #1 to #n is performed for the currents $I_1$ to $I_n$ applied to the measurement points #1 to #n, the procedure of frequency analysis in the frequency analyzing section 7 shown in FIG. 1 becomes tangled, and thus the analysis result becomes inaccurate. Therefore, for performing the same signal processing as that for the voltages $V_1$ to $V_n$ in the measurement points #1 to #n, the high pass filters $67_1$ to $67_n$, the programmable gain amplifiers $68_1$ to $68_n$, and the low pass filters $69_1$ to $69_n$ are necessitated. The amplification ratio of the programmable gain amplifiers $63_1$ to $63_n$ and $68_1$ to $68_n$ can be controlled by control signals 211 and 212 sent from the controlling section 20.

In the present invention, procedures and means for signal processing performed for the measured currents and the measured voltages are not limited. As long as accurate frequency analysis can be realized in the frequency analyzing section 7, any procedure and any means may be used for the signal processing. The currents $I_1$ to $I_n$ respectively applied to the measurement points #1 to #n and the voltages $V_1$ to $V_n$ in the respective measurement points that are measured as above are converted to digital signals by the A/D converters $70_1$ to $70_n$ and $65_1$ to $65_n$, and the converted digital signals are sent to the frequency analyzing section 7.

In the frequency analyzing section 7 shown in FIG. 1, frequency analysis is made for the currents $I_1$ to $I_n$ respectively applied to the skin of the measurement points #1 to #n and the voltages $V_1$ to $V_n$ in the skin of the respective measurement points #1 to #n, and based on the frequency analysis result, the frequency response of the skin impedance directly under the respective measurement points #1 to #n are calculated. The principle thereof will be hereinafter described. The description will be given on the assumption that the skin impedance does not depend on the applied current density, and the skin can be regarded as a linear system. When the current applied to the skin of the subject is current i(t) as shown in the following Mathematical formula (1) and the skin can be assumed as the linear system, a voltage generated in the skin by current application is expressed as voltage v(t) as shown in the following Mathematical formula (2).

[Mathematical Exp. 1]

$$i(t) = \sum_n \sqrt{2} |I_n| \sin(\omega_n t + \theta_{i_n}) \tag{1}$$

$$v(t) = \sum_n \sqrt{2} |V_n| \sin(\omega_n t + \theta_{v_n}) \tag{2}$$

where $\omega$ is $2\pi f$ (f is a measurement frequency), $|In|$ and $|Vn|$ are respectively actual values of a current and a voltage of each frequency component, and $\theta_{i_n}$ and $\theta_{v_n}$ are respectively phases of the current and the voltage of each frequency component fn. When Fourier transform of i(t) and v(t) in Mathematical formulas (1) and (2) are expressed as $I(j\omega)$ and $V(j\omega)$, the following formulas are established.

[Mathematical Exp. 2]

$$I(j\omega) = \sum_n \sqrt{2\pi} |I_n|(\cos\theta_{i_n} - j\sin\theta_{i_n})\delta(\omega - \omega_n) \tag{3}$$

$$= \sum_n (R_{I_n}(\omega) - jX_{I_n}(\omega)) \cdot \delta(\omega - \omega_n)$$

$$V(j\omega) = \sum_n \sqrt{2\pi} |V_n|(\cos\theta_{v_n} - j\sin\theta_{v_n})\delta(\omega - \omega_n) \tag{4}$$

$$= \sum_n (R_{V_n}(\omega) - jX_{V_n}(\omega)) \cdot \delta(\omega - \omega_n)$$

$\delta(\omega)$: Dirac delta function

Thus, the skin impedance $Z(j\omega)$ can be expressed by the following formula.

[Mathematical Exp. 3]

$$Z(j\omega) = \sum_n (R_{Z_n} - jX_{Z_n}) \cdot \delta(\omega - \omega_n) \tag{5}$$

where the following formulas are established.

[Mathematical Exp. 4]

$$R_{Z_n} = \frac{R_{I_n}(\omega)R_{V_n}(\omega) + X_{I_n}(\omega)X_{V_n}(\omega)}{R_{I_n}^2(\omega) + X_{I_n}^2(\omega)} \tag{6}$$

$$X_{Z_n} = \frac{R_{I_n}(\omega)X_{V_n}(\omega) - X_{I_n}(\omega)R_{V_n}(\omega)}{R_{I_n}^2(\omega) + X_{I_n}^2(\omega)} \tag{7}$$

That is, when a plurality of necessary frequencies fn are included in i(t), i(t) and v(t) are provided with Fourier transform, and thereby the impedance in each frequency can be obtained based on each real part and each imaginary part. In addition, when the frequency included in the current waveform is an integer multiple of the lowest frequency fmin, spectrum leakage to the adjacent frequencies when discrete Fourier transform is provided does not exist, and the lower limit of the time resolution is determined only depending on the lowest frequency. Therefore, the skin impedance locus can be measured with the high time resolution.

Figure 3:
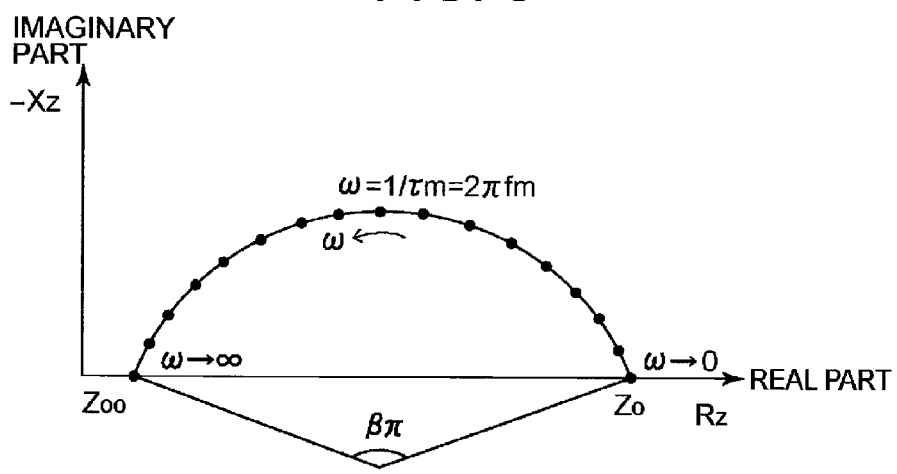
FIG. 3 is an explanation diagram explaining Cole-Cole circular arc's law.
Figure 4:
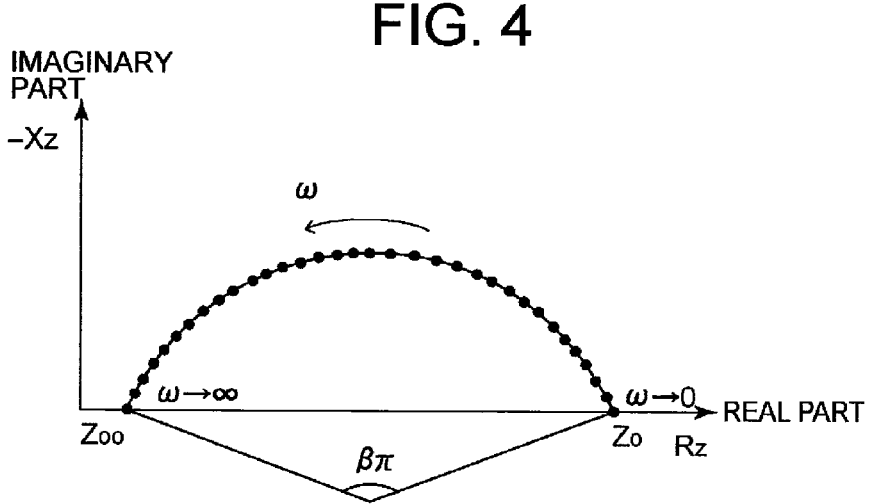
FIG. 4 is a diagram explaining that measurement data distributes uniformly on the impedance locus.
Figure 5:
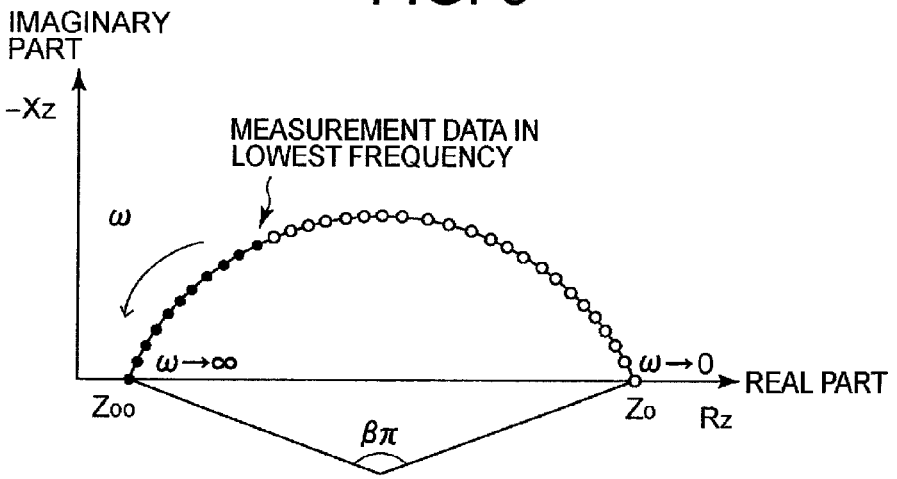
FIG. 5 is a diagram explaining that measurement data distributes partially on the impedance locus in an unbalanced manner.

It is known that the skin impedance $Z(j\omega)=R_Z(\omega)-jX_Z(\omega)$ satisfies Cole-Cole circular arc's law expressed by the following Mathematical formula (9), and a locus on the complex plane of the frequency response is distributed on the circular arc as shown in FIG. 3.

[Mathematical Exp. 5]

$$Z(j\omega) = R_Z(\omega) - jX_Z(\omega) \qquad (8)$$

$$= Z_\infty + \frac{Z_0 - Z_\infty}{1 + (j\omega\tau_m)^\beta} \qquad (9)$$

where $\omega$ is $2\pi f$ (f is a measurement frequency), $\tau_m$ is a parameter representing a central relaxation time, $\beta$ is a parameter representing a central angle of the circular arc, and the following Mathematical formula is established.

[Mathematical Exp. 6]

$$Z_0 = \lim_{\omega \to 0} Z(\omega), \; Z_\infty = \lim_{\omega \to \infty} Z(\omega)$$

In general, in the case of the skin impedance, the impedance in the high frequency region is extremely small, and thus $Z\infty \approx 0$ may be assumed. When Mathematical formula (9) is expressed not with the use of the angle frequency $\omega$ but with the use of the frequency f, the following formulas are established.

[Mathematical Exp. 7]

$$Z(jf) = R_Z(f) - jX_Z(f) \qquad (10)$$

$$= Z_\infty + \frac{Z_0 - Z_\infty}{1 + (j2\pi f \tau_m)^\beta} \qquad (11)$$

$$= Z_\infty + \frac{Z_0 - Z_\infty}{1 + \left(j\dfrac{f}{fm}\right)^\beta} \qquad (12)$$

$fm=1/2\pi\tau_m$ is called characteristics frequency. Though Mathematical formula (9) is equivalent to Mathematical formula (12), a description will be hereinafter given with the use of Mathematical formula (12).

In some cases, Cole-Cole circular arc's law is not satisfied even when the locus on the complex plane of the frequency response of the measured skin impedance distributes on the circular arc. A general skin impedance including such a case can be expressed by the following Mathematical formulas (13) and (14) in which another parameter $\alpha$ is added to the foregoing Mathematical formula (12).

[Mathematical Exp. 8]

$$Z(jf) = R_Z(f) - jX_Z(f) \qquad (13)$$

$$= Z_\infty + \frac{Z_0 - Z_\infty}{1 + j^\beta(2\pi f \tau_m)^\alpha} = Z_\infty + \frac{Z_0 - Z_\infty}{1 + j^\beta\left(\dfrac{f}{fm}\right)^\alpha} \qquad (14)$$

As an example not satisfying Cole-Cole circular arc's law, a case in which the skin impedance depends on the measurement current density and skin is not able to be regarded as the linear system can be cited. In the conventional example, the parameter that does not largely depend on the contact state of the measurement electrodes and clearly reflects the electric characteristics difference between the acupuncture point and the other regions is noted. Specifically, the conventional example is based on the assumption that the measured skin impedance satisfies Cole-Cole circular arc's law. Out of 4 parameters ($Z_0$, $Z_\infty$, $\beta$, and $\tau_m = 2\pi/fm$) in Mathematical formula (12), the central relaxation time $\tau_m$ in Cole-Cole circular arc's law is noted. Based on the difference of the parameter $\tau_m$, the acupuncture point is determined. As described before, in the conventional example, however, the following problems exist.

A means for confirming whether or not Cole-Cole circular arc's law is satisfied in the measured skin impedance is not provided.

The procedure for inferring the central relaxation time $\tau_m$ is tangled.

Measurement data does not distribute uniformly on the skin impedance locus.

Therefore, confirmation is previously made that the skin impedance in the respective measurement points #1 to #n calculated in the frequency analyzing section 7 do not depend on the measurement current density. After that, the acupuncture point position is determined in a determining section 9. Thereby, confirmation can be made indirectly whether or not Cole-Cole circular arc's law is satisfied in the measured skin impedance. Therefore, the reliability and the reproducibility of a characteristics amount generated in a characteristics amount generating section 8 can be higher than those of the conventional example.

Further, in the characteristics amount generating section 8, frequency response K(f) as a ratio between real part RZ(f) and imaginary part XZ(f) of the skin impedance Z(jf) is calculated based on the frequency response of the skin impedance Z(jf) sent from the frequency analyzing section 7, and K(f0) in fixed frequency f0 set by the controlling section 20 is generated for every measurement point. Such K(f0) is employed as an evaluation parameter instead of the parameter $\tau_m$ in the conventional example. Thereby, the procedure for inferring the parameter is not tangled. In addition, the size of such K(f) has a positive correlativity with the size of the parameter $\tau_m$ noted in the conventional example. Therefore, in the same manner as in the conventional example, the acupuncture point can be determined based on the difference of the evaluation parameter that does not largely depend on the contact state of the measurement electrodes that are the current application electrodes $3_1$ to $3_n$, the earth electrode 4, and the minus electrode 5, and clearly reflects the electric characteristics difference between the acupuncture point and the other regions. For the reason thereof, a description will be hereinafter given. First, when Mathematical formula (14) is deformed, the following Mathematical formulas (15) and (16) can be obtained.

[Mathematical Exp. 9]

$$\frac{R_Z(f) - Z_\infty}{Z_0 - Z_\infty} = \frac{1 + (2\pi f \tau_m)^\alpha \cos\dfrac{\beta\pi}{2}}{1 + 2(1\pi f \tau_m)^\beta \cos\dfrac{\beta\pi}{2} + (\omega\tau_m)^{2\beta}} \qquad (15)$$

$$= \frac{1 + (f/f_m)^\alpha \cos\dfrac{\beta\pi}{2}}{1 + 2(f/f_m)^\beta \cos\dfrac{\beta\pi}{2} + (f/f_m)^{2\beta}}$$

-continued $$\frac{X_Z(f)}{Z_0 - Z_\infty} = \frac{(2\pi f \tau_m)^\alpha \sin\frac{\beta\pi}{2}}{1 + 2(2\pi f \tau_m)^\alpha \cos\frac{\beta\pi}{2} + (\omega\tau_m)^{2\beta}} \quad (16)$$

$$= \frac{(f/f_m)^\alpha \sin\frac{\beta\pi}{2}}{1 + 2(f/f_m)^\alpha \cos\frac{\beta\pi}{2} + (f/f_m)^{2\beta}}$$

When the skin impedance satisfies Cole-Cole circular arc's law and the skin impedance in the high frequency region can be regarded as 0, that is, when $\alpha = \beta$ and $Z_\infty = 0$ are satisfied, the foregoing Mathematical formulas (15) and (16) can be expressed by the following Mathematical formulas (17) and (18).

[Mathematical Exp. 10]

$$\frac{R_Z(f)}{Z_0} = \frac{1 + (2\pi f \tau_m)^\beta \cos\frac{\beta\pi}{2}}{1 + 2(2\pi f \tau_m)^\beta \cos\frac{\beta\pi}{2} + (2\pi f \tau_m)^{2\beta}} \quad (17)$$

$$= \frac{1 + (f/f_m)^\beta \cos\frac{\beta\pi}{2}}{1 + 2(f/f_m)^\beta \cos\frac{\beta\pi}{2} + (f/f_m)^{2\beta}}$$

$$\frac{X_Z(f)}{Z_0} = \frac{(2\pi f \tau_m)^\beta \sin\frac{\beta\pi}{2}}{1 + 2(2\pi f \tau_m)^\beta \cos\frac{\beta\pi}{2} + (2\pi f \tau_m)^{2\beta}} \quad (18)$$

$$= \frac{(f/f_m)^\beta \sin\frac{\beta\pi}{2}}{1 + 2(f/f_m)^\beta \cos\frac{\beta\pi}{2} + (f/f_m)^{2\beta}}$$

The ratio $K(f)$ ($K(f) = XZ(f)/RZ(f)$) between the real part $RZ(f)$ and the imaginary part $XZ(f)$ in Mathematical formulas (17) and (18) is expressed by the following Mathematical formula (19).

[Mathematical Exp. 11]

$$K(f) = \frac{X_Z(f)}{R_Z(f)} \quad (19)$$

$$= \frac{(2\pi f \tau_m)^\beta \sin\frac{\beta\pi}{2}}{1 + (2\pi f \tau_m)^\beta \cos\frac{\beta\pi}{2}}$$

$$= \frac{(f/f_m)^\beta \sin\frac{\beta\pi}{2}}{1 + (f/f_m)^\beta \cos\frac{\beta\pi}{2}}$$

Therefore, when $\beta$ is constant, the size of $K(f)$ in the same measurement frequency f has a positive correlativity with the size of $\tau_m$. Meanwhile, in this case, the size of $K(f)$ in the same measurement frequency f has a negative correlativity with the size of fm.

To effect the foregoing description, $\beta$ should be constant and $Z_\infty$ should be 0. It is known that in general, in the case of the skin impedance, $\beta$ falls within the range from 0.65 to 0.9, that is, within the extremely limited range. In addition, when the areas of the measurement electrodes 3, 4, and 5 are identical and the measurement points #1 to #n are comparatively adjacent to each other, $\beta$ can be regarded as an almost constant value. Further, the size of the skin impedance in the high frequency region is smaller than that in the low frequency region. In particular, in the case of the skin impedance measured by the foregoing 3 electrode method, the size of the skin impedance in the high frequency region is extremely small. Thus, $Z_\infty$ may be regarded as 0.

In this embodiment, in the characteristics amount generating section 8, for example, the current I generated from the current generating section 1 includes a frequency component of one frequency f0, and the ratio K(f0) between the real part and the imaginary part of the skin impedance is calculated for each of the measurement points #1 to #n. In the determining section 9, determination is made that the measurement point in which K(f0) becomes a value lower than those of the other measurement points is the acupuncture point. Thereby, the acupuncture point can be determined with the use of the hardware structure simpler than that of the conventional example, based on the difference of the evaluation parameter that does not largely depend on the contact state of the measurement electrodes 3, 4, and 5 and clearly reflects the electric characteristics difference between the acupuncture point and the other regions. Further, the foregoing K(f0) is the value only for a given fixed frequency f0. Thus, differently from in the conventional example in which the parameter $\tau_m$ is directly and precisely obtained, it is not necessary to measure the skin impedance in the wide range including extremely low frequencies.

In the foregoing determination method, the description has been given of the case that the frequency included in the current I is only f0. However, the invention is not limited thereto. As long as K(f0) of a given frequency clearly reflects the electric characteristics difference between the acupuncture point and the other regions, such a frequency can be included in the current I, and the number of frequencies included in the current I is not limited. For example, the following method may be employed. In the current generating section 1, the current I including a plurality of frequency components is previously generated. Out of the foregoing plurality of frequency components, the frequency with the value of K(f) significantly showing the difference among the respective measurement points #1 to #n is selected in the characteristics amount generating section 8. Then, K(f) of such a frequency is sent to the determining section 9. Thereby, the reliability of determining the acupuncture point position in the determining section 9 can be more improved with the use of a simple hardware configuration. In addition, it is possible to confirm whether or not the above-mentioned assumptions for $\beta$ and $Z_\infty$ are satisfied.

$fm = \tau_m/2\pi$ in Mathematical formula (19) is a frequency in which the absolute value of the imaginary part XZ is the maximum value. Therefore, the characteristics amount generated in the characteristics amount generating section 8 may be the frequency fm in which the absolute value of the imaginary part XZ of the frequency response of the skin impedance calculated in the frequency analyzing section 7 is the maximum value. In this case, the determining section 9 may determine that the point in which fm becomes larger than that of the other measurement points is the acupuncture point. Thereby, the acupuncture point can be determined with the use of the hardware structure simpler than that of the conventional example, based on the difference of the evaluation parameter that does not largely depend on the contact state of the measurement electrodes 3, 4, and 5 and clearly reflects the electric characteristics difference between the acupuncture point and the other regions. The characteristics amount in the respective measurement points #1 to #n generated in the characteristics amount generating section 8 as described above and the determination result in the determining section 9 are sent to a display section 10, and displayed by a display means such as a monitor as appropriate.

INDUSTRIAL APPLICABILITY

As described above, in the acupuncture point position evaluating apparatus according to the present invention, whether or not Cole-Cole circular arc's law is satisfied in the measured skin impedance can be confirmed, and the procedure for calculating the characteristics amount used for evaluation is simple. Further, the reliability and the reproducibility of the measurement result can be improved more than those of the conventional example. In addition, the characteristics amount used for the evaluation has a correlativity with the central relaxation time $\tau_m$ in Cole-Cole circular arc's law as a conventionally noted parameter. Therefore, the acupuncture point can be determined based on the difference of the evaluation parameter that does not largely depend on the contact state of the measurement electrodes, and clearly reflects the electric characteristics difference between the acupuncture point and the other regions. In result, the acupuncture point position can be determined with the higher reliability and the higher reproducibility with the use of the hardware structure simpler than that of the conventional example. Consequently, the acupuncture point position evaluating apparatus according to the present invention is useful for noninvasively and objectively evaluating the electric characteristics difference of skin in the medical field such as determining acupuncture stimulation effects, searching for a position of a stimulation point called acupuncture point, and searching for a ryodo point (good electroconductive point) in acupuncture treatment or the like.

The invention claimed is:

1. A skin impedance attenuation point position evaluating apparatus comprising:
    a current generating section for generating a current composed of at least one frequency component;
    an electrode system for applying the current from the current generating section to a plurality of different measurement points on skin by a plurality of electrodes to be arranged on the skin of a living body;
    current detectors for detecting the currents respectively applied to the plurality of measurement points;
    a measuring section for measuring the currents detected by the current detectors and a voltage generated in the skin at each of the plurality of measurement points by current application by the electrode system;
    a frequency analyzing section for performing frequency analysis for both the currents and the voltages measured by the measuring section, and obtaining frequency response of a skin impedance in each of the respective measurement points;
    a characteristics amount generating section for generating a characteristics amount of the skin impedance in each of the respective measurement points based on the frequency response of the skin impedance in each of the plurality of measurement points that are analyzed by the frequency analyzing section;
    a determining section for determining a skin impedance attenuation point position based on the characteristics amount in the respective measurement points generated by the characteristics amount generating section; and
    a display means for displaying the characteristics amount in each of the respective measurement points generated by the characteristics amount generating section and the skin impedance attenuation point position determined by the determining section,
    wherein said plurality of electrodes includes a first electrode and a plurality of measuring point electrodes so that said application of said output current is performed by concurrently applying the same between said first electrode and each of said measuring point electrodes,
    wherein said current detectors concurrently detect the currents respectively applied to said measuring point electrodes, and
    wherein said measuring section includes a second electrode to be arranged on said skin so that the voltage between said second electrode and each of said measuring point electrodes is concurrently detected using a voltage of said first electrode as a reference voltage.

2. The skin impedance attenuation point position evaluating apparatus according to claim 1, wherein the frequency analyzing section comprises means for determining whether or not Cole-Cole circular arc's law is satisfied in the frequency response of the skin impedance in the respective measurement points.

3. The skin impedance attenuation point position evaluating apparatus according to claim 1, wherein the current generated in the current generating section includes one lowest frequency component and a frequency component that is an integer multiple of the lowest frequency.

4. The skin impedance attenuation point position evaluating apparatus according to claim 1, wherein the current generating section can change a size of the frequency component included in the applied current for every frequency and for every measurement position.

5. The skin impedance attenuation point position evaluating apparatus according to claim 1, wherein the characteristics amount generated in the characteristics amount generating section is a ratio between a real part and an imaginary part of the skin impedance in at least one frequency.

6. The skin impedance attenuation point position evaluating apparatus according to claim 1, wherein for each of the plurality of measurement point the characteristics amount generating section determines a ratio between a real part and a imaginary part of the skin impedance in at least one frequency, and wherein out of each of said ratios the characteristics amount generating section selects the ratio of a frequency in which a difference thereof among the respective measurement points is significant as the characteristics amount.

7. The skin impedance attenuation point position evaluating apparatus according to claim 1, wherein the characteristics amount generated in the characteristics amount generating section is a ratio between a real part and an imaginary part of the skin impedance in a lowest frequency included in the applied current.

* * * * *